United States Patent [19]

Davidson

[11] Patent Number: Plant 6,147

[45] Date of Patent: Apr. 12, 1988

[54] ROSE PLANT NAMED "SMOOTH LADY"

[75] Inventor: Harvey D. Davidson, Orinda, Calif.

[73] Assignee: Gurney Seed and Nursery Corporation, Yankton, S. Dak.

[21] Appl. No.: 823,585

[22] Filed: Jan. 28, 1986

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—L. S. Van Landingham, Jr.

[57] ABSTRACT

A new rose variety of the hybrid tea class distinctive in its character by being thornless and by blooms of a high-centered pink color as hereafter shown and described.

1 Drawing Sheet

The present invention relates to a new and distinct variety of rose plant of the hybrid tea rose class, which was originated by my crossing "Smooth Sailing" (Little Darling×Pink Favorite) as the seed parent crossed with unnamed seedling ((Polly×Peace)×Circus)) as pollen parent.

Among the novel characteristics possessed by this new variety which distinguish it from its parents and all other varieties of which I am aware are: (1) Neither thorns nor prickles on the main stems, laterals or leaf stems. (2) An attractive upright plant habit with good glossy leaf density. (3) A medium sized, pointed, pink flower which repeats rapidly.

Asexual reproduction of the new rose variety by budding, as performed at McFarland, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.) The terminology used in color description herein refers to plate numbers in the aforementioned color chart, e.g. "55A" is plate "55A" of The Royal Horticultural Society Colour Chart.

American Rose Society Registration commercial appellation "Smooth Lady".

Irar and Ciopora appellation "Hadlady".

Parentage: Seedling.

*Seed parent.*—"Smooth Sailing".

*Pollen parent.*—((Polly×Peace)×Circus)). p0

Class: Hybrid tea.

The following observations are made of specimens grown outdoors in Contra Costa County, Calif. in the month of October.

FLOWER

Blooming Habit

A. Bud:

(1) *Size.*—Medium to long.

(2) *Form.*—Slender and tapering.

(3) *Sepals.*—Pronounced extension of serrated foliaceous appendages extending about 1.5 cm beyond tip of bud. Color before breaking — 144A, when turned down — 146C.

(4) *Peduncle.*—Length — 5 to 6 cm; Surface — smooth, no prickles or hairs; Strength — Slender but sturdy; Color — 144B, flushed 172B.

(5) *Color.*—When sepals first divide — 46B; at base of petal slight yellow — 13A. As petals unfurl — 52A.

B. Bloom:

(1) *Size.*—Average when open — 10–11 cm.

(2) *Borne.*—Singly, occasionally two or three to stem.

(3) *Form.*—Pointed high center. Petals unfurl with roll upon opening. Rapid open to loose at maturity.

(4) *Petalage.*—Number of petals under normal conditions — 22 to 26.

(5) *Color.*—Early open stages: Outer side of petals — 52A, inner side — 52C. Fully open: outer petals — 55A, petals towards center — 55B. Veining on inside of petals — 47D. Slight yellow at base of petal — 10A. Color changing as bloom ages to 55C.

C. Petals:

(1) *Texture.*—Thick.

(2) *Appearance.*—Satiny on inside, shiny on outside.

(3) *Form.*—Broad, ovoid.

(4) *Arrangement.*—Regular to loose.

(5) *Petaloids in center.*—Few.

(6) *Persistence.*—Drop off cleanly.

(7) *Fragrance.*—Strong fruit.

(8) *Lasting quality.*—Moderate on plant, long lasting as cut flower.

REPRODUCTIVE ORGANS

A. Stamen:

(1) *Arrangement.*—Regularly arranged around styles.

(2) *Number.*—Average 100 to 110.

(3) *Length.*—Average 7–10 mm.

(4) *Filaments.*—Color 47A.

(5) *Anthers.*—Color 20A.

(6) *Pollen.*—Color 24B; Viable.

B. Pistil:

(1) *Styles.*—Covered with fine white hairs. Some shading of color 47A.

(2) *Stigma.*—Color 27B.

(3) *Ovary.*—Bulbous, well developed.

C. Hips:

(1) *Shape.*—Globular; Average diameter — 2.5-3 cm.

(2) *Color.*—33B when mature.

(3) *Seed.*—Average 12-16 per hip; Do not protrude.

PLANT

A. Form: Upright.

B. Growth: Very vigorous; many main stems from base of plant.

*Height.*—1.5 meter.

C. Foliage: Compound of 3 to 5 leaflets on bloom stem, 5 to 7 leaflets on main canes, few 7.

(1) *Size.*—Large.

(2) *Quantity.*—Abundant. Stems fully covered.

(3) *Color.*—New foliage: Upper side 144A, lower side 146B. Old foliage: Upper side 147A, lower side 146A.

(4) *Shape.*—Elliptical and pointed.

(5) *Texture.*—Upper side: leathery and glossy, Under side: smooth and dull.

(6) *Edge.*—Uniform small serration.

(7) *Rachis.*—Smooth both upper and lower sides; reddish turning green when mature.

(8) *Stipules.*—Medium length with long beard.

D. Wood: (1) New wood: Color — 172A; Bark — smooth. (2) Old wood: Color — 146C; Bark — smooth.

E. Thorns: No thorns or prickles on main stems, laterals, rachis or peduncle.

F. Resistance to disease:

*Mildew.*—Excellent.

*Rust.*—Slight towards end of growing season.

*Blackspot.*—None observed.

G. Winter hardiness: Good winter hardiness.

I claim:

1. A new and distinct variety of rose plant of the hybrid tea class, substantially as shown and described, characterized by its lack of thorns or prickles at any point on the plant which is upright, well covered with glossy foliage which is disease resistance and having well formed pink flowers coming one to three to a blooming stem which repeat rapidly.

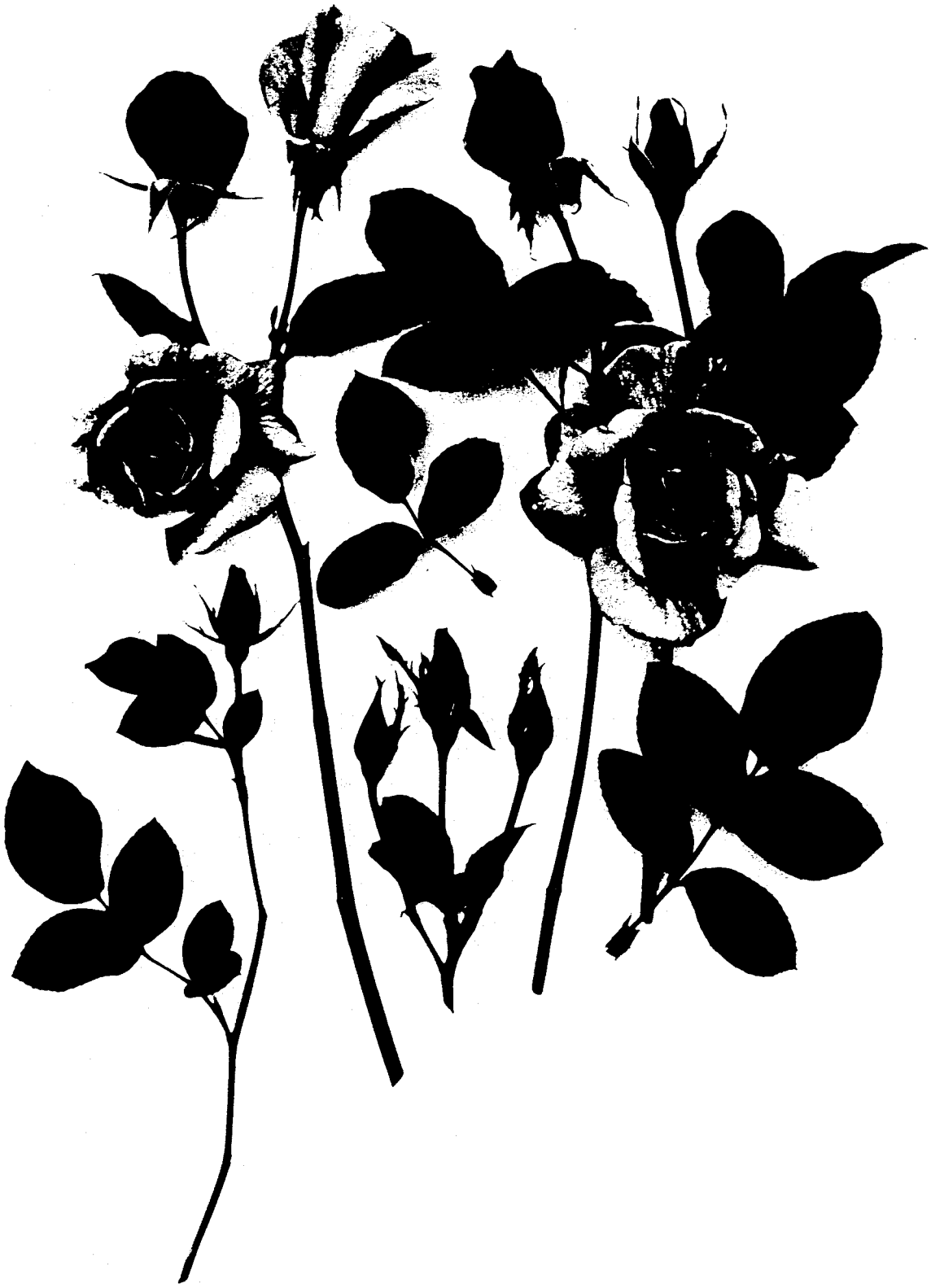

* * * * *